US005403345A

United States Patent [19]

Spingler

[11] Patent Number: 5,403,345
[45] Date of Patent: Apr. 4, 1995

[54] NEEDLE SUTURE ATTACHMENT
[75] Inventor: Rolf A. Spingler, Jestetten, Germany
[73] Assignee: United States Surgical Corporation, Norwalk, Conn.
[21] Appl. No.: 135,111
[22] Filed: Oct. 12, 1993
[51] Int. Cl.6 .............................................. A61B 17/04
[52] U.S. Cl. ................................... 606/224; 606/225; 606/226
[58] Field of Search ................................ 606/222–227

[56] References Cited

U.S. PATENT DOCUMENTS

| 86,769 | 2/1869 | Marriott . |
| 295,612 | 3/1884 | Bailey . |
| 299,305 | 5/1884 | Weed . |
| 877,476 | 1/1908 | Bach . |
| 1,106,667 | 8/1914 | Minahan . |
| 1,250,114 | 12/1917 | Chapin . |
| 1,558,037 | 10/1925 | Morton . |
| 1,591,021 | 7/1926 | Davis . |
| 1,613,206 | 1/1927 | Souttar . |
| 1,665,216 | 4/1928 | Morton et al. . |
| 1,678,361 | 7/1928 | Shearon . |
| 1,757,129 | 5/1930 | McClure . |
| 1,960,117 | 5/1934 | Lydeard . |
| 1,981,651 | 11/1934 | Logan . |
| 2,022,234 | 11/1935 | Everett . |
| 2,240,330 | 4/1941 | Flagg et al. . |
| 2,302,986 | 11/1942 | Vollrath . |
| 2,411,079 | 11/1946 | Baule ............................ 606/226 |
| 2,802,468 | 8/1957 | Everett . |
| 2,814,296 | 11/1957 | Everett . |
| 2,910,983 | 11/1959 | Everett . |
| 2,928,395 | 3/1960 | Forbes et al. . |
| 3,311,110 | 3/1967 | Singerman et al. . |
| 3,394,704 | 7/1968 | Dery . |
| 3,799,169 | 3/1974 | Beroff et al. . |
| 3,835,912 | 9/1974 | Kristensen et al. . |
| 3,875,946 | 4/1975 | Duncan . |
| 3,880,167 | 4/1975 | Hardwick . |
| 3,890,975 | 6/1975 | McGregor ..................... 606/227 |
| 3,910,282 | 10/1975 | Messer et al. . |
| 3,918,455 | 11/1975 | Coplan . |
| 3,924,630 | 12/1975 | Walldorf . |
| 3,926,194 | 12/1975 | Greenberg et al. . |
| 3,943,933 | 3/1976 | Gertzman . |
| 3,949,756 | 4/1976 | Ace . |
| 3,963,031 | 6/1976 | Hunter ........................... 606/227 |
| 3,980,177 | 9/1976 | McGregor . |
| 3,981,307 | 9/1976 | Borysko . |
| 4,054,144 | 10/1977 | Hoffman et al. . |
| 4,072,041 | 2/1978 | Hoffman et al. . |
| 4,124,027 | 11/1978 | Boss ............................... 606/227 |
| 4,127,133 | 11/1978 | Martinez . |
| 4,672,734 | 6/1987 | Kawada et al. . |
| 4,901,722 | 2/1990 | Noguchi ......................... 606/224 |
| 5,046,350 | 9/1991 | Proto et al. . |
| 5,099,676 | 3/1992 | Proto et al. . |
| 5,131,131 | 7/1992 | Proto et al. . |
| 5,168,619 | 12/1992 | Proto et al. . |
| 5,207,701 | 5/1993 | West ............................... 606/226 |

OTHER PUBLICATIONS

United States Pharmacopeia, Edition XXII, (1990) pp. 1614–1615.

Primary Examiner—Gary Jackson

[57] ABSTRACT

A needle suture combination and attachment method is disclosed wherein a surgical suture is attached to a surgical needle by inserting the suture tip into a tapered axial hole formed in the barrel section through the needle blunt end face and swaging the needle barrell section. The swage commences at a point away from the end of the needle end face. The needle suture attachment of the invention does not require closely corresponding suture and needle hole diameters, and advantageously achieves reliable needle-suture attachment with reduced needle inventory. Process and equipment maintenance are also reduced.

18 Claims, 2 Drawing Sheets

NEEDLE SUTURE ATTACHMENT

TECHNICAL FIELD

The present invention relates to surgical needles, and more specifically to an improved needle-suture attachment and method.

BACKGROUND OF THE INVENTION

Surgical sutures customarily are attached to a metallic surgical needle in order to facilitate use of the suture-needle combination during a surgical procedure. Pull out forces for permanent and removable needles are defined in the United States Pharmacopoeia XXII (1990), hereby incorporated by reference.

Sutures historically have been attached to needles by swaging or crimping the suture into the blunt end of the needle. In one known method, a channel is formed in the barrel end of the needle by splitting the barrel longitudinally. The suture tip is placed into the channel and the channel is crimped to grip and hold the suture tip to the needle. In another known attachment method, a cylindrical hole is drilled along the longitudinal axis of the needle and through the end face of the needle barrel section. The drilled hole generally is formed by mechanical or laser drilling. As shown in FIG. 1, in this attachment method a suture tip 1 is inserted into the drilled hole 2 and the barrel end of the needle is swaged or crimped in a region 3 which extends a distance from the end face 4 of the needle sufficient to securely hold the suture to the needle. This attachment method suffers from several drawbacks. One disadvantage is that crimping the needle barrel end out to the end face 4 brings the needle bore edge 5 in close contact with the suture, potentially creating a weakened suture portion immediately adjacent the needle suture attachment. More specifically, during suturing the needle may be angled relative to the suture, effectively causing the needle bore edge 5 to cut into and potentially weaken the suture tip 1. Furthermore, in order to obtain the desired attachment, the needle bore diameter, suture tip diameter and swaging or crimping force must be balanced to achieve the desired holding force. Because a wide variety of suture size and needle combinations are desired, the manufacturer must maintain a large inventory of various needle sizes and configurations having different bore hole diameters, and must standardize attachment dies, procedures and equipment to repeatedly provide consistent attachments. Of course, swaging equipment is subject to wear and variability during use, so careful attention must be paid to equipment maintenance if consistent swaging force and, hence, needle suture attachment is to be obtained. For example, if insufficient inward swaging force is applied by the die to the needle barrel, the compression gripping of the needle on the suture may be insufficient and the suture may pull out from the needle under too little force to meet specification. Conversely, where excessive inward swaging force is applied, the excessive compression gripping force exerted on the suture causes the suture tip to become crushed and weakened, thereby reducing the strength of attachment and the suture pull out force.

In view of these and other shortcomings of traditional needle suture attachment methods and apparatus, it would be desirable to provide a needle suture attachment which substantially eliminates the risk of a needle bore edge cutting into and weakening the suture. In addition, it would be desirable to provide a needle suture attachment method and apparatus which reduces the inventory of needles which must be maintained to facilitate attachment of multiple suture sizes to different needles, and provides consistent attachment with reduced maintenance and waste.

In addition, it would be desirable to provide a needle configuration which facilitates connection to a variety of suture sizes so as to reduce the inventory of needles which must be maintained. Further, it would be desirable to provide a needle construction which can be attached to a variety of suture sizes using substantially the same swaging force without the need to adjust swaging equipment or processes, thereby reducing needle attachment process and equipment maintenance. Finally, it would be desirable to provide a needle construction and attachment which have reduced sensitivity to variations in swaging force.

SUMMARY OF THE INVENTION

In accordance with the invention a surgical needle is provided having a tip section, a body section and a barrel section. The barrel section includes a blunt end face with an axial hole extending into the needle barrel section along the longitudinal axis of the needle. The axial hole has a diameter at the blunt end face which is less than the diameter of the needle at the blunt end. The axial hole tapers radially inwardly from the needle blunt end face to a reduced diameter distal to the blunt end face. Preferably, the edge of the axial hole at the opening in the blunt end is rounded.

A surgical needle-suture combination is provided wherein a needle having a tapered axial hole is swaged about the tip of a surgical suture to hold the suture in the needle. The suture may be made of any biocompatible material, and may be absorbable or nonabsorbable. Suitable absorbable materials include surgical gut materials or synthetic absorbable polymers or copolymers of such materials as glycolide, lactide, caprolactone, dioxanone, trimethylene carbonate, etc. Suitable nonabsorbable materials include nylon, silk, polypropylene, polyethylene terathalate, polyester, polytetrafluoroethylene, etc. The swage may be formed so as to provide a permanently attached needle or a removable needle, as defined in United States Pharmacopoeia, XXII, and preferably provides a permanently attached needle. The swage preferably commences at a point away from the blunt end face of the needle and terminates away from the bottom of the needle bore hole proximal to the end face from the hole bottom in order to reduce stresses on the needle which can result from inward swaging force at the bottom of the hole and cause premature failure of the needle.

In the method of the invention a tapered axial hole is formed in the blunt end face of a surgical needle, a surgical suture tip is inserted into the tapered axial hole and the needle is swaged about the suture to join the suture to the needle. The swaged area is formed so as to commence at a point away from the blunt end face and terminates at a point not aligned with the bottom of the needle bole hole.

The needle and needle-suture combination of the invention advantageously permit needles having a single configuration of needle hole to be attached to a range of sutures of different diameters. In addition, the configuration of the tapered axial hole facilitates attachment of each suture to the needle with the approximately the same inward swage force to obtain needle-suture combinations having consistently high pull-out force. Because the swage terminates away from the needle blunt end face and the bottom of the axial hole premature failure of the needle-suture juncture is substantially reduced. In addition to the foregoing advantages, the fact that numerous suture sizes can be attached to a single needle configuration having a tapered bore hole in accordance with the present invention means that in-process needle inventory can be substantially reduced.

BRIEF DESCRIPTION OF THE DRAWINGS

The accompanying drawings, referred to herein and constituting a part hereof, illustrate preferred embodiments of the present invention.

DETAILED DESCRIPTION OF THE PREFERRED EMBODIMENTS

Figure 1:
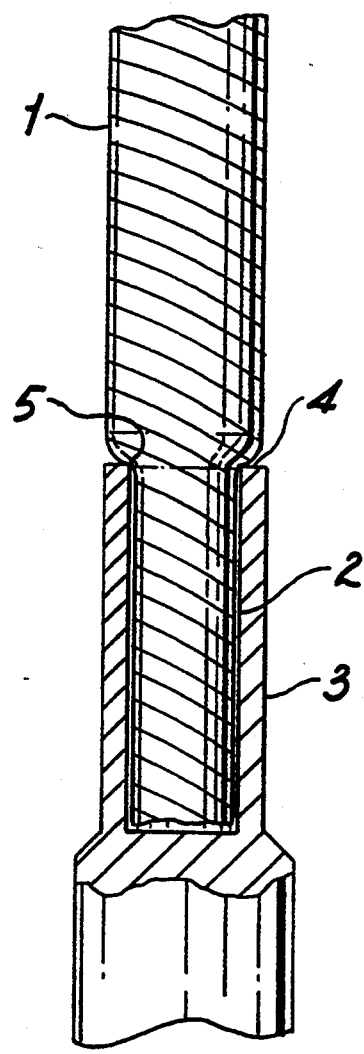
FIG. 1 is a partial side cross sectional view of a needle attached to a suture in accordance with a prior art needle suture swaging method.
Figure 2:
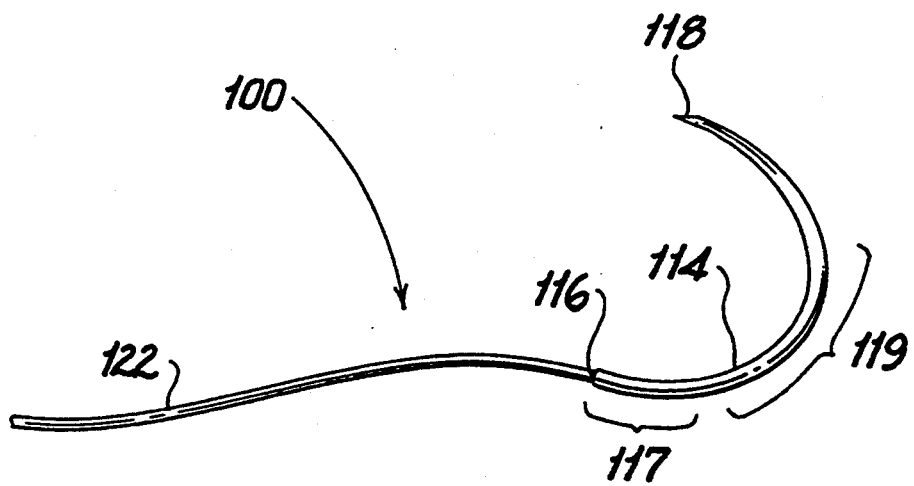
FIG. 2 is a perspective view of a needle suture combination in accordance with the present invention.

Referring now to the drawings, there is shown a needle suture combination device 1 00 generally consisting of a suture 122 and a needle 114 (see FIG. 2 ). The suture may be monofilament or multifilament construction, and may be made from absorbable or nonabsorbable materials. In the case of multifilament sutures such sutures usually are tipped with a tipping agent in a known manner to prevent brooming which can interfere with insertion of the suture tip into the needle. The needle may be made of any suitable biocompatible material and typically is made of metal, such as stainless steel, e.g., 300 or 400 series stainless steel. As shown in FIG. 2, needle 14 may be of curved configuration, but it should be understood that the needle may be straight or curved and may be tapered with a blunt, ball or sharp tip and/or one or more cutting edges, etc. For the purpose of the present description, the end of the needle into which the suture is inserted shall be referred to as the blunt end face 116, with the immediately adjacent section of the needle being referred to as the barrel section 117. The sharp end or needle tip 118 is located at the opposite end of the needle distal to the blunt end. In general, the region between the tip and barrel section constitutes the body section 19 of the needle. In cross-section, the body section may be, inter alia, round, triangular, square or rectangular. Appropriate transition zones between the various sections of the needle may be provided. Of course, the foregoing description should not be construed to require that all such needles be sharp, pointed, tapered, etc.

Figure 3:
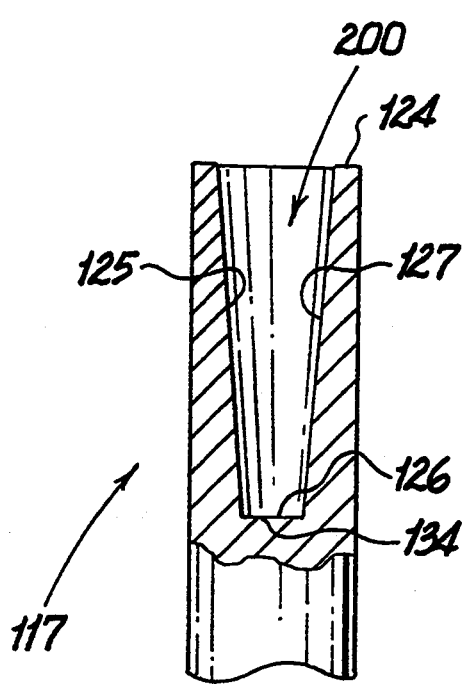
FIG. 3 is a partial side cross sectional view of a needle having an axial tapered hole drilled in the barrel section of the needle.
Figure 4:
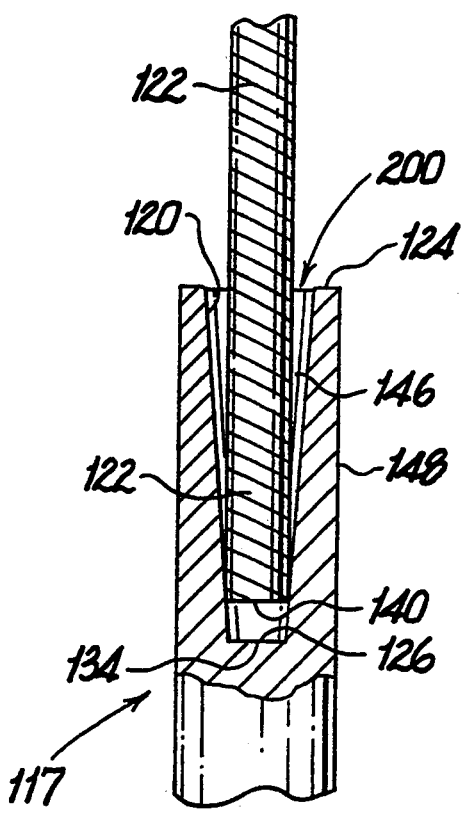
FIG. 4 is a partial side cross sectional view of a suture tip disposed in the open end of surgical needle having a tapered hole drilled in the barrel section of the needle.
Figure 5:
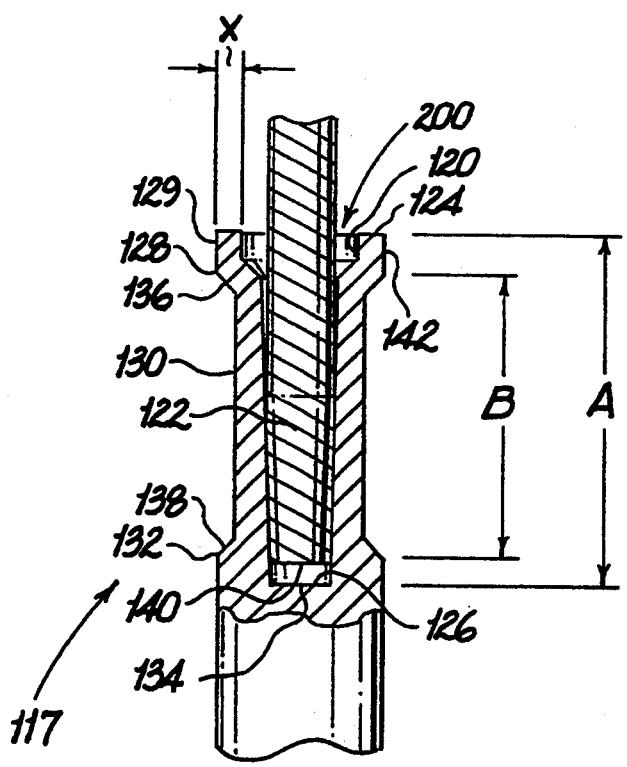
FIG. 5 is a partial side cross sectional view of the needle of FIG. 4 with the largest size suture to be attached to the needle swaged to the needle barrel section so as to attach the needle to the suture in accordance with the invention.

In one embodiment of the invention shown in FIGS. 3-5, the needle barrel section 117 has an axial hole or bore 200 formed through the needle end face 124 and extending longitudinally into the barrel section 117. The needle bore 200 may be formed in any suitable manner such as mechanical or laser drilling. Needle bore 200 preferably is configured as a tapered hole having a pair of oppositely positioned tapered walls 125,127, a maximum diameter at needle end face 124 and a minimum diameter at the needle bore bottom 126 distal to needle end face 124. Needle bore bottom 126 preferably terminates at a bore bottom surface 134 having a diameter approximating the diameter of the smallest suture size to be attached to the needle. Referring now to FIG. 4, the needle 114 of FIGS. 2 and 3 is shown with a suture tip 122 inserted into the needle bore 200 with the suture tip end 140 disposed toward needle bore bottom 126. As can be seen from FIG. 4, the relatively wide width of the needle bore 200 at needle end face 124 facilitates insertion of the suture tip 122 into the needle bore 200. As will be appreciated from FIG. 4, sutures having different suture tip diameters will be insertable into bore 200 to different depths determined by the point at which the diameter of tapered hole 146 matches the suture tip 122 diameter.

Referring to FIG. 5, the needle 114 of FIGS. 3 and 4 is shown after having been swaged to a suture tip 122 in accordance with the invention. As shown, the swage commences at a point 128 located a distance from needle end face 124 so as to provide an unswaged portion 142 of barrel end 129 adjacent end face 124. The swaged region 130 is substantially uniform over its length and defines a substantially uniform compression reducing the needle diameter in the swaged region 130 by about 10 to about 20 percent of the preswaged needle diameter and preferably about 10 to about 15 percent of the pre-swaged needle diameter. The substantially uniform swaged region 130 terminates at a needle bore edge 132 distal to needle end face 124. As will be explained in detail below, swaged region 130 preferably terminates prior to needle bore bottom 126. Thus, the needle bore edge 132 does not press against and potentially weaken the suture adjacent the needle, and there is little, if any, likelihood the needle bore edge will cut into the suture during use. Configuring the swage in this manner avoids weakening of the needle wall which can result from terminating the swage at the bottom of the needle hole.

It will be understood that, as shown in FIGS. 2 and 5, a taper or blend 136, 138 occurs at points 128 and 132, respectively, to provide transition to and from the full needle diameter to the lesser diameter of swaged region 130. By way of example only, a 3 degree blend or transition can be provided in a known manner by appropriately configuring the swaging die.

Since the needle bore 200 is tapered, a swaged region 130 of substantially constant outer diameter is formed with the swaged needle bore 200 having a varying inner diameter. This results in the swage having an increasing degree of compression over the internal length A of needle bore 200. Thus, a maximum degree of compression is achieved slightly away from the needle bore bottom 126 and toward the needle end face 124 while the minimum swage compression is achieved where swage region 130 meets tapers 136, 138. The degree of compression decreases over the length B of the swage region 130 from the needle bore bottom 126 to tapers 136, 138. The extent of compression near the needle bore bottom 126 is selected to appropriately compress and secure the smallest size suture to be attached to the needle. Conversely, the degree of compression adjacent taper or blend 136 is selected, as appropriate, to secure the largest suture to be attached to the needle.

Figure 6:
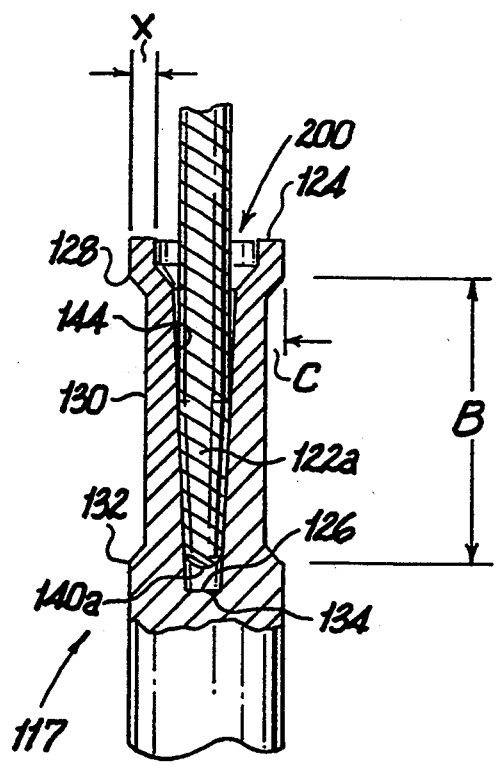
FIG. 6 is a partial side cross sectional view of a needle having a tapered hole with the smallest size suture to be attached to the needle swaged to the needle barrel section so as to attach the needle to the suture in accordance with the invention.

Thus, when the smallest suture 122a is attached to the needle, as shown in FIG. 6, the depth or degree of compression C adjacent needle bore bottom 126 compresses the suture tip 140a to the appropriate degree to attach the suture 122 to the needle barrel 117. As shown, over a portion of the length B of the swage region 130 the needle bore walls 144 do not contact the suture 122a. As shown in FIG. 5, when the larger suture 122 to be attached to the needle barrel 117 is disposed in the needle bore hole 200 and the swage is made, appropriate compression to secure the suture 122 to the needle 117 occurs in the swage region 130 near taper 136. As will be appreciated, the degree of compression of a large suture 122 which occurs toward needle bore bottom 126 will exceed the degree of compression appropriate for holding the suture 122 to the needle 117; that is, overswaging will occur in this region. Overswaging is generally believed to be undesirable since damage to the suture can result and cause an undesirable decrease in the pull out force required to separate the suture from the needle. With the suture needle attachment of the present invention, however, overswaging or overcrimping distal to the needle end face 124 is immaterial since a sufficient degree of swaging, and therefore suture compression, occurs at a point along the length B of the swage region 130 closer to the needle end face 124. That is, as long as an appropriate compression occurs at a point along the length of the swage region 130 any overswaging that occurs toward the needle bore bottom 126 and any underswaging that occurs toward the open end 120 of the needle bore 200 are immaterial. The swage attachment of the present invention consistently achieves proper needle-suture attachment with consistent suture pull-out force since the appropriate degree of swaging is always achieved at some point along the swage region.

As will be appreciated, the needle attachment of the present invention advantageously provides manufacturing flexibility with respect to needle-suture attachment. Because a needle of a given diameter and configuration, e.g., curved, cutting, reverse cutting, etc., can be provided with a tapered bore hole, a multiplicity of the needles of the same configuration which vary only in needle bore diameter can be eliminated in favor of one or a few tapered needle bore configurations. This reduces production inventory and associated labor, material and storage costs. In addition, because it is not critical to achieve a precise degree of compression while simultaneously avoiding overswaging over the entire swage region, manufacturing tolerances are more forgiving. This results in less waste and higher productivity since equipment maintenance and testing will occur less often. For example, for all but the largest of sutures slight overswaging of the needle of the present invention will still result in proper compression and attachment at a point toward the open end of the needle bore.

The present invention is useful for needle-suture attachments of all sizes and combinations, and may find particular application to attachment of very small needles to suture, e.g., sutures of size 7/0 and smaller. In attaching such needles and sutures it is difficult to form a proper hole in the needle, insert a very small suture tip into the hole, and achieve precisely the appropriate degree of compression of the suture by swaging to result in a needle-suture attachment having the appropriate suture pull out force. In addition, such fine sutures are particularly susceptible to overswaging and breakage at the needle bore opening due to nicking or cutting by the edge of the needle bore opening. With the needle attachment of the present invention, however, the tapered needle bore hole provides a relatively large target for insertion of the needle and greater flexibility in swaging is provided, resulting in more consistent production of acceptable needle sutures. In addition, because the swage area does not extend to the end of the needle, there is reduced likelihood of nicking or cutting of the suture at the edge of the needle bore.

The tapered needle hole may be formed by a variety of methods known to those skilled in the art. For example, the hole may be mechanically drilled using a drill bit having a tapered configuration. Alternatively, the hole may be formed by laser drilling by adjusting the laser pulse to result in greater removal of material near the bore opening than at the bottom of the needle bore.

In the preferred method of the present invention a suture tip 140 is inserted into a tapered needle bore 200 until the suture tip 140 contacts either the needle bore bottom 126 or the tapered walls 125, 127 of the needle bore 200, the contact depending upon the diameter of the suture 117 relative to the needle bore taper 146. Thereafter, the needle bore 200 is swaged such that the swage commences at a point 128 located a distance away from the needle end face 124 and includes a tapered swage region 130 extending from the initial commencement of the swage to a maximum swage point 132 distal from the needle end face 124. Such a tapered swage region 130 may be achieved by swaging the needle barrel section 117 with a needle bore taper 146 so as to provide a swaged region 130 having a substantially constant diameter along the outer wall 148 of the needle barrel section 117 because of the tapered hole configuration a constantly increasing degree of swaging compression over the length of the swaging region B from the commencement 128 of swage region proximal to the needle blunt end face toward the needle bore bottom 126. The attachment method of the present invention further is unique in that a portion of the swage region 130 may knowingly or intentionally be overswaged and overcompress a portion of the suture tip 122 without adversely affecting removal of the needle barrel section 117 from the suture tip 122. Such a result is contrary to accepted wisdom which dictates that overswaging must always be avoided.

As a further advantage of the invention swaging may be performed using a conventional swaging die having a lead in of approximately 3 degrees on either side of the swage region 130. Such dies are readily available and do not require special tooling requirements.

While the foregoing description contains many specifics, the present invention is not limited to such specifics. To the contrary, it will be understood that numerous changes, modifications and alterations to the apparatus and method disclosed herein will occur to those of ordinary skill in the art. The invention in its broader aspects is not limited to the detailed disclosure, and the invention, including any such changes, modifications and alterations shall be evaluated with respect to the scope of the appended claims.

What is claimed is:

1. A surgical needle-suture combination comprising:
   a surgical needle having a barrel section with an unexpanded outer diameter, a blunt end face and an axial hole in said barrel section extending longitudinally from said blunt end face into said barrel section, said axial hole having a first diameter at said blunt end face and being tapered along a continuous wall to a second, reduced diameter at the bottom of the hole away from said blunt end face; and
   a surgical suture, one end of said suture disposed in said axial hole and said needle swaged about said suture to uniformly reduce the outer diameter of a portion of the barrel section to attach said suture to said needle with increasing compression away from said blunt end face, a portion of the suture adjacent the bottom of the hole being overswaged and an attachment portion between said overswaged portion and said blunt end face being compressed to attach said suture to said needle.

2. The needle-suture combination of claim 1 wherein said suture is a braided suture.

3. The needle-suture combination of claim 2 wherein the end of said suture disposed in said axial hole is tipped with a tipping agent.

4. The needle-suture combination of claim 1 wherein said suture is made of a bioabsorbable material.

5. The needle-suture combination of claim 1 wherein said suture is made of a non-absorbable material.

6. The needle-suture combination of claim 1 wherein said needle swage terminates a distance from said blunt end face.

7. The needle-suture combination of claim 1 wherein said needle swage terminates away from the bottom of said axial hole.

8. The needle-suture combination of claim 7 wherein said needle swage terminates distal to the bottom of said axial hole relative to the blunt end face.

9. The needle-suture combination of claim 1 wherein said tapered axial hole of said swaged needle includes a region between said compressed suture portion and said blunt end face not in swaged contact with said suture.

10. The needle-suture combination of claim 1 wherein said swaged portion has a diameter of from about 10 to about 20 percent less than the diameter of the unswaged barrel section.

11. A method of making a surgical needle-suture combination comprising:
   providing a surgical needle having a barrel section with an outer diameter and a blunt end face and an axial hole in said barrel section extending longitudinally from said blunt end face into said barrel section, said axial hole having a first diameter at the blunt end face and being uniformly tapered along a continuous wall to a second, reduced diameter at the bottom of the hole distal to said blunt end face;
   inserting the tip of a surgical suture into said axial hole; and
   swaging said needle about said suture to uniformly compress a portion of the barrel section to an outer diameter less than the outer diameter of the unswaged barrel section, thereby compressing the suture tip within the hole with increasing compression toward the bottom of the hole to said needle to said suture.

12. The method of claim 11 wherein said step of inserting said suture into said axial hole comprises inserting said suture into said axial hole until the end of said suture contacts said tapered walls of said needle.

13. The method of claim 12 wherein said swaging step comprises swaging said needle so that the swage terminates a distance away from the bottom of said axial hole.

14. The method of claim 13 wherein said swaging step comprises swaging said needle so that the swage terminates proximal of the bottom of said axial hole.

15. The method of claim 11 wherein said step of swaging said needle comprises swaging the needle such that a portion of the suture tip toward the bottom of the hole is overswaged with a portion of the suture between the blunt end face and the overswaged portion being compressed to attach said needle to said suture.

16. A surgical needle-suture combination comprising:
   a surgical needle having a barrel section with an outer diameter, a blunt end face and an axial hole in said barrel section extending longitudinally from said blunt end face into said barrel section, said axial hole having a first diameter at said blunt end face and being tapered along a continuous wall to a second, reduced diameter at the bottom of the hole away from said blunt end face; and
   a surgical suture, one end of said suture disposed in said axial hole and said needle swaged about said suture to uniformly reduce the outer diameter of a portion of the barrel section to provide a swaged region to attach said suture to said needle, said swaged region having a substantially uniform outer diameter which is less than the outer diameter of the unswaged barrel section, a portion of the suture toward the bottom of the hole being overswaged and a portion of the suture at a point between said blunt end face and said overswaged portion being compressed to attach said suture to said needle.

17. The needle-suture combination of claim 16 wherein said swaged portion has a diameter of from about 10 to about 20 percent less than the diameter of the unswaged barrel section.

18. The needle-suture combination of claim 16 wherein said swaged portion of said needle includes a region between said compressed suture portion and said blunt end face not in swaged contact with said suture.

* * * * *